Feb. 7, 1956 C. S. SHAMBURGER Plant Pat. 1,456
ROSE PLANT
Filed March 24, 1955
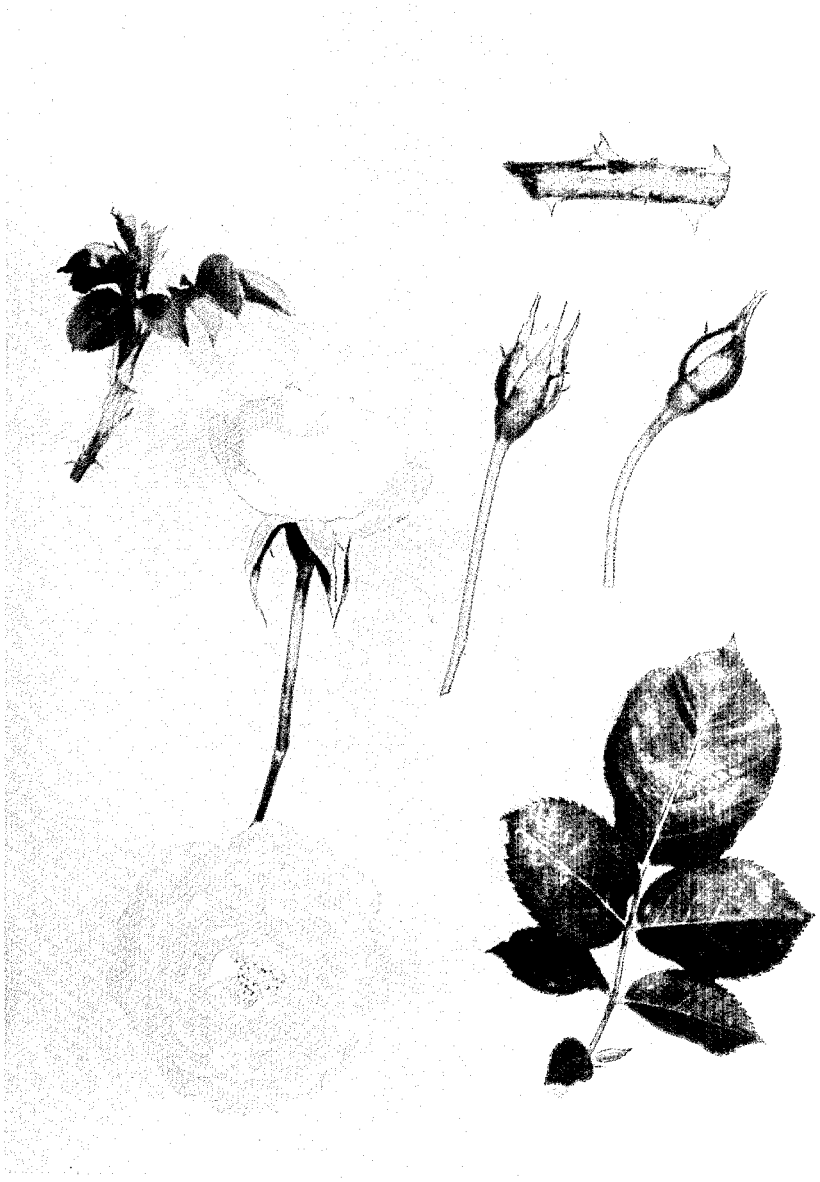
Inventor.
C. S. Shamburger
By: Robb & Robb
Attorneys.

United States Patent Office

Plant Pat. 1,456
Patented Feb. 7, 1956

1,456

ROSE PLANT

Carl S. Shamburger, Tyler, Tex., assignor to C. W. Stuart & Co., Newark, N. Y., a corporation of New York Application March 24, 1955, Serial No. 496,627

1 Claim. (Cl. 47—61)

The present invention relates to a new and distinct variety of rose plant which was discovered by me as a sport of the variety known as "Cavalcade" (Plant Patent No. 991) which I was growing on property under my direction and control near Tyler, Texas.

At the time of my discovery, I had a block of the variety "Cavalcade" under cultivation, and my attention was directed to one plant on which there appeared an unusual pink bloom which definitely was quite different from the regular blooms of this variety. Continued observations and subsequent asexual reproduction of the pink sport by budding and also by cuttings, as made by me in the regular course of my commercial nursery operations near Tyler, Texas, showed that the unique characteristic of the pink sport came true to form and was established and transmitted through succeeding propagations.

My observations and tests further showed that the new variety has a distinct 2-tone effect of pink and silvery iridescent white, there being a contrast between the inside and the outside of the petals, as in the case of the parent variety, but the contrast being of entirely different colors as compared with those of the parent variety. In the bud stage, the color effect of my new variety is pink, with a light yellow diffusion. As the flower opens, the effect is that of a deep pink color, with a silvery color diffused with light yellow on the reverse of the petals, these colors changing to light silvery pink with a silvery white reverse as the flower matures. These color changes progress from day-to-day, and are definitely not color changes produced by fading. In all stages of the open flower, the flower has an entirely different appearance when viewed from above, as compared with that when viewed from the side.

Another distinction is found in the fragrance of the flowers of my new variety when compared with that of its parent and other hybrid polyantha roses. The flowers do not have the fruity fragrance of those of the parent variety, but instead, have a clear, sweet fragrance that is quite pronounced even at a substantial distance therefrom.

Except for the outstanding distinguishing characteristics noted above, the new variety has inherited most of the principal characteristics of its parent variety "Cavalcade," and altogether, the characteristics and distinctions of the new variety definitely differentiate the same from its parent variety "Cavalcade," as well as from all other varieties of which I am aware, and my tests and reproductions of the new variety have conclusively proved that the characteristics and distinctions are fully established and transmissible by asexual reproduction.

The accompanying drawing shows typical specimens of the vegetative growth and flowers of my new variety in different stages of development and as depicted in color as nearly true as it is reasonably possible to make the same in a color illustration of this character.

The following is a general description of my new variety, with color terminology in accordance with the Horticultural Color Chart issued by the British Color Council in collaboration with the Royal Horticultural Society, except where general color terms of ordinary dictionary significance are obvious:

Type: Hardy; tall; bush; sport; for cut flowers and for garden decoration.
Class: Hybrid polyantha (floribunda).
Breeding: Sport of "Cavalcade."
Propagation: Holds its distinguishing characteristics through succeeding propagations by cuttings and by budding.

FLOWER

Locality where grown and observed: Near Tyler, Smith County, Texas, and Newark, New York.
Flowers borne: Usually several to stem; on strong stems of medium length; in pyramidal cluster.
Quantity of bloom: Abundant, both outdoors and in greenhouse.
Continuity: Continuous.
Fragrance: Strong; sweet.
Bud:
*Peduncle.*—Medium length; medium caliper; erect; prickly; medium smoothness. Color—reddish green.
*Before calyx breaks.*—Size—small. Form—short; pointed; ovoid; with a conspicuous neck; without foliaceous appendages on the surface of the bud; without entire foliaceous parts extending beyond the tip of the bud. Color—Solferino Purple, Plate 26/2.
*As calyx breaks.*—Color—Solferino Purple, Plate 26/2.
*As first petal opens.*—Size—medium. Form—ovoid. Color: Outside—upper ⅓ Mimosa Yellow, Plate 602/3, suffused with Solferino Purple, Plate 26/3; lower ⅔ Aureolin, Plate 3/1. Inside—upper ⅔ Solferino Purple, Plate 26/1; lower ⅓ Aureolin, Plate 3/1.
*Opening.*—Opens up well.
Bloom:
*Size (when fully open).*—Large; from 2½ inches to 3 inches.
*Petalage.*—Very double; from 28 to 32 petals.
*Form.*—Cupped; full; petals being at first rolled inward, but becoming tightly rolled outward at maturity.
Petals: Thick; inside shiny velvety; outside shiny velvety.
*Shape.*—Outside—obovate, with apex flat and with 1 notch. Intermediate—obovate, with apex flat and with 1 notch. Inside—obovate, with apex flat and with 1 notch.

This description of a newly opened flower was made from a rose grown outdoors, in the month of September, at Newark, New York:

*Color.*—Outside petal: Outside surface—upper ⅔ silvery iridescent white, with base of Mimosa Yellow, Plate 602/2; inside surface—upper ⅔ Solferino Purple, Plate 26/1, with base of Aureolin, Plate 3/1. Intermediate petal: Outside surface—upper ⅔ silvery irridescent white, with base of Mimosa Yellow, Plate 602/2; inside surface—upper ⅔ Solferino Purple, Plate 26/1, with base of Aureolin, Plate 3/1. Inner petal: Outside surface—upper ⅔ silvery iridescent white, with base of Mimosa Yellow, Plate 602/2; inside surface—upper ⅔ Solferino Purple, Plate 26/1, with base of Aureolin, Plate 3/1.

This description was made from a rose that was open for 5 days outdoors in the month of September, at Newark, New York:

*Color.*—Outside petal: Outside surface—upper ⅔ silvery iridescent white, with base of Mimosa Yellow, Plate 602/3; Inside surface—Solferino Purple, Plate 26/3, with tips of silvery white. Inside petal: Outside surface—upper ⅔ silvery iridescent white, with base of Mimosa Yellow, Plate 602/3; inside surface—Solferino Purple, Plate 26/3, with tips of silvery white.

*General color effect.*—Newly opened flower—2-toned Aureolin and Solferino Red. 3-days open—Solferino Red and silver.

*Behavior.*—Drop off cleanly.

*Flower longevity.*—On bush in garden—5 days in September. Cut flowers grown indoors and kept at living-room temperatures—5 days in September.

REPRODUCTIVE ORGANS

Stamens: Medium quantity; regularly arranged about pistils.

Filaments: Medium length; most with anthers.

*Color.*—Light yellow.

Anthers: Medium size; open at various times.

*Color.*—Yellowish brown.

Pollen: Moderate.

*Color.*—Gold.

Pistils: Many.

Styles: Even; long; thin; bunched.

Stigma:

*Color.*—Yellow.

Ovaries: All enclosed in calyx.

Hips: Short; ovoid; with inconspicuous neck; smooth; thick walls.

*Color.*—Green-gray.

Sepals: Permanent; long; curled.

*Color.*—Light yellow.

Seeds: Many; medium size.

PLANT

Foliage:

*Leaves.*—Compound of 5 leaflets; moderately abundant; medium size; leathery; glossy.

*Leaflets.*—Oval, with apex acute; base obtuse; margin serrate.

*Color.*—Mature: Upper surface—dark green-bronze; under surface—light green. Young: Upper surface—green-bronze; under surface—light green.

*Rachis (the supporting stem of the compound leaf).*—Heavy. Upper side—smooth. Under side—hairy.

*Stipules.*—Medium length; with medium length points turning out at an angle of less than 45°.

*Disease resistance.*—Better than average resistance to mildew and blackspot, as determined by comparison with other varieties grown under comparable cultural conditions at Newark, New York, and in Smith County, Texas.

Growth:

*Habit.*—Bushy; much-branched.

*Growth.*—Vigorous.

*Canes.*—Moderately heavy.

*Main stems.*—Color—green-bronze. Thorns—few; hooked downward; with long, broad base. Prickles — few; color — green. Hairs — several; color—green.

*Branches.* — Color — green-bronze. Thorns—few; hooked downward; with long, broad base. Prickles—few; color—reddish green. Hairs—several; color—green.

*New shoots.*—Color—green-brown. Thorns—few; long; hooked downward; with broad base. Prickles—few; color—green-brown. Hairs—several; color—green.

I claim:

A new and distinct variety of rose plant of the hybrid polyantha class, substantially as herein shown and described, characterized particularly as to novelty by its general similarity to the variety "Cavalcade" (Plant Patent No. 911), except for its unique and distinctive 2-toned flowers, the color effect of which is pink diffused with light yellow in the bud stage thereof, said bud color changing to deep pink with silvery reverse diffused with light yellow, and then to light silvery pink with silvery white reverse as the flower opens and matures, and the strong, clear sweet fragrance of the flowers which is quite pronounced even at a substantial distance from the flowers.

No references cited.